(12) United States Patent
Hsiu

(10) Patent No.: US 9,901,263 B2
(45) Date of Patent: Feb. 27, 2018

(54) RADIAL ARTERY BLOOD PRESSURE WAVEFORM MEASURING DEVICE

(71) Applicant: National Taiwan University of Science and Technology, Taipei (TW)

(72) Inventor: Hsin Hsiu, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 307 days.

(21) Appl. No.: 14/807,898

(22) Filed: Jul. 24, 2015

(65) Prior Publication Data

US 2016/0120419 A1   May 5, 2016

(30) Foreign Application Priority Data

Nov. 4, 2014 (TW) .............................. 103138158 A

(51) Int. Cl.
*A61B 5/02* (2006.01)
*A61B 5/021* (2006.01)
*A61B 5/00* (2006.01)

(52) U.S. Cl.
CPC ........ *A61B 5/02141* (2013.01); *A61B 5/6831* (2013.01); *A61B 2562/14* (2013.01)

(58) Field of Classification Search
CPC .............. A61B 5/02141; A61B 5/6831; A61B 2562/14; A61B 5/021; A61B 5/022
See application file for complete search history.

(56) References Cited

U.S. PATENT DOCUMENTS

| 3,095,873 | A | * | 7/1963 | Edmunds, Jr. | ......... A61B 5/022 600/499 |
| 4,090,504 | A | * | 5/1978 | Nathan | .............. A61B 5/02055 128/DIG. 15 |
| 4,830,017 | A | * | 5/1989 | Perry | ..................... A61B 5/021 600/485 |

(Continued)

FOREIGN PATENT DOCUMENTS

| CN | 101077300 A | 11/2007 |
| CN | 103429169 A | 12/2013 |

OTHER PUBLICATIONS

Hsin Hsiu et al., "Effects of acupuncture on the harmonic components of the radial arterial blood-pressure waveform in stroke patients ", IOS Press of Biorheology 50 (2013) 69-81, accepted in revised form Mar. 4, 2013.

(Continued)

*Primary Examiner* — Tiffany Weston
*Assistant Examiner* — Tho Tran
(74) *Attorney, Agent, or Firm* — CKC & Partners Co., Ltd.

(57) ABSTRACT

A radial artery blood pressure waveform measuring device includes a stress sensor, a stress concentrating elastic structure, and a stress guiding elastic member. The stress sensor is in contact with a skin surface of a wrist corresponding to a position of a radial artery. The stress concentrating elastic structure is disposed on the stress sensor. The stress guiding elastic member has a top surface, a bottom surface, and at least one side surface. The bottom surface is disposed on the stress concentrating elastic structure, and an area of the bottom surface is greater than an area of a horizontal section of the stress concentrating elastic structure.

8 Claims, 2 Drawing Sheets

(56) References Cited

U.S. PATENT DOCUMENTS

| | | | | |
|---|---|---|---|---|
| 4,901,733 A * | 2/1990 | Kaida | ............... | A61B 5/021 600/485 |
| 5,101,829 A * | 4/1992 | Fujikawa | ............... | A61B 5/022 600/485 |
| 5,179,956 A * | 1/1993 | Harada | ............... | A61B 5/02233 600/485 |
| 5,240,007 A * | 8/1993 | Pytel | ............... | A61B 5/021 600/485 |
| 5,467,771 A * | 11/1995 | Narimatsu | ............... | A61B 5/021 600/485 |
| 6,491,647 B1 * | 12/2002 | Bridger | ............... | A61B 5/021 128/900 |
| 2005/0234351 A1 * | 10/2005 | Nishii | ............... | A61B 5/02 600/503 |
| 2009/0247885 A1 * | 10/2009 | Suzuki | ............... | A61B 5/02416 600/500 |
| 2010/0049010 A1 | 2/2010 | Goldreich | | |
| 2011/0048138 A1 * | 3/2011 | Li | ............... | B81B 3/0086 73/721 |

OTHER PUBLICATIONS

Chao-Tsung Chen et al.,"Using a blood pressure harmonic variability index to monitor the cerebral blood flow condition in stroke patients ", IOS Press of Biorheology 48 (2011) 219-228, accepted in revised form Aug. 13, 2011.

Chia-Liang Hsu et al.,"Characteristics of harmonic indexes of the arterial blood pressure waveform in polycystic ovary syndrome", Lippincott Williams & Wilkins of Analytical methods and statistical analysis, accepted Feb. 28, 2014.

* cited by examiner

RADIAL ARTERY BLOOD PRESSURE WAVEFORM MEASURING DEVICE

RELATED APPLICATIONS

This application claims priority to Taiwan Application Serial Number 103138158, filed Nov. 4, 2014, which is herein incorporated by reference.

BACKGROUND

Technical Field

The present disclosure relates to a blood pressure waveform measuring device, and more particularly, to a radial artery blood pressure waveform measuring device.

Description of Related Art

The physiological measurement of blood pressure provides important diagnostic information to medical practitioners regarding the state of a patient's circulatory and cardiac systems. Techniques for measuring blood pressure include invasive and non-invasive methods. A typical invasive technique involves inserting a catheter directly into the artery to be monitored, and measuring the pressure induced on a column of fluid within the catheter with an external pressure transducer. A typical non-invasive blood pressure measurement technique involves determining blood pressure by sensing blood pressure waveform (BPW) data derived from an artery. As varying pressure is applied to the artery by, for example, an air bag or a chamber, blood pressure waveforms are sensed by a transducer, and these waveforms are converted into sensed blood pressure waveform data. The sensed blood pressure waveform data is then analyzed to determine waveform parameters which relate to the shape of the sensed blood pressure waveforms.

However, the current non-invasive blood pressure waveform measurement techniques may cause discomfort to the patient. Therefore, there is a need to provide a non-invasive blood waveform measuring device with a novel mechanism.

SUMMARY

According to some embodiments of the disclosure, a radial artery blood pressure waveform measuring device is provided. The radial artery blood pressure waveform measuring device includes a stress sensor, a stress concentrating elastic structure, and a stress guiding elastic member. The stress sensor is in contact with the skin surface of a wrist corresponding to a position of a radial artery. The stress concentrating elastic structure is disposed on the stress sensor. The stress guiding elastic member has a top surface, a bottom surface, and at least one side surface. The bottom surface is placed upon the stress concentrating elastic structure, and an area of the bottom surface is greater than an area of a horizontal section of the stress concentrating elastic structure.

By sequentially applying the contractile force on the stress guiding elastic member, the stress concentrating elastic structure, and the stress sensor by the elastic band, the stress sensor is properly positioned on the skin surface of the wrist at a place corresponding to the radial artery, such that the measurement can be performed accurately.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 1:
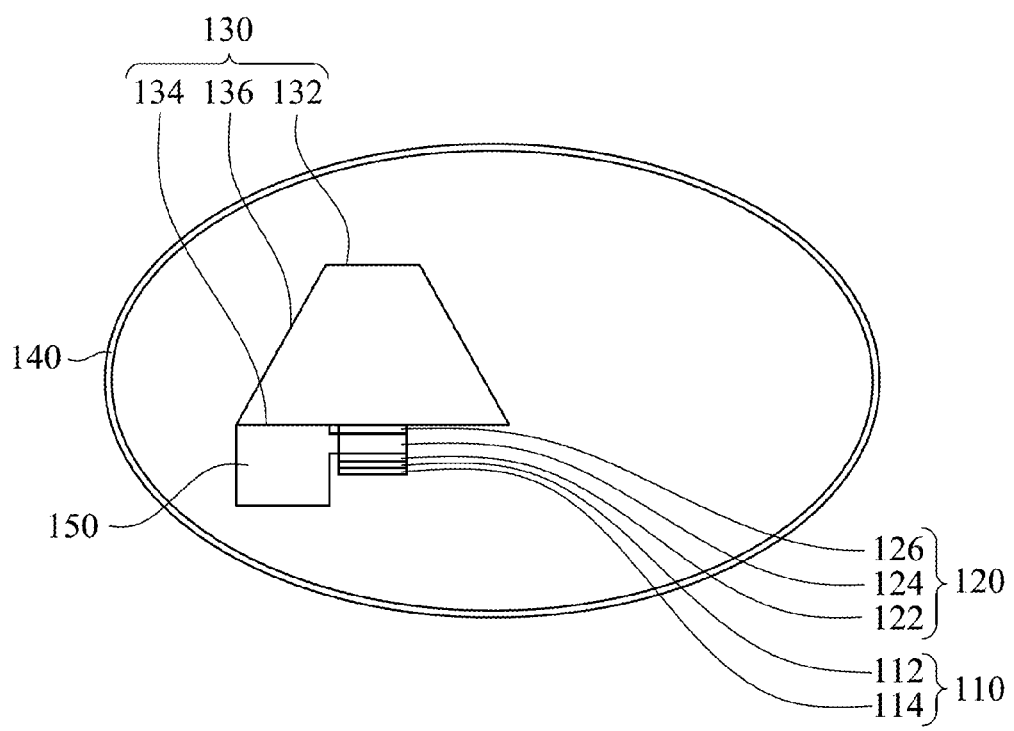
FIG. 1 is a schematic front view of a radial artery blood pressure waveform measuring device according to one embodiment of this invention.
Figure 2:
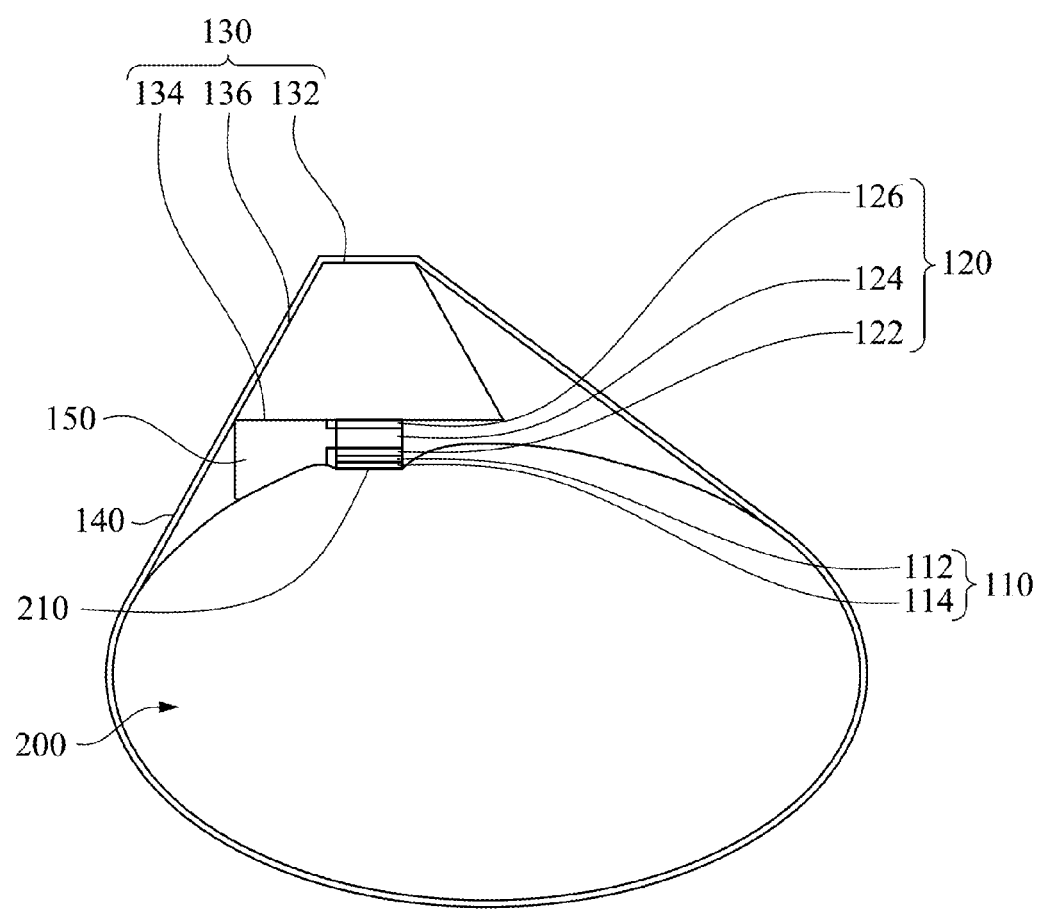
FIG. 2 is a schematic front view of the radial artery blood pressure waveform measuring device of FIG. 1 shown in a state fixed to a wrist.

FIG. 1 is a schematic front view of a radial artery blood pressure waveform measuring device 100 according to one embodiment of this invention. FIG. 2 is a schematic front view of the radial artery blood pressure waveform measuring device 100 of FIG. 1 shown in a state fixed to a wrist 200. As shown in FIGS. 1 and 2, a radial artery blood pressure waveform measuring device 100 is provided. The radial artery blood pressure waveform measuring device 100 measures the waveform of the blood pressure of the radial artery, and the radial artery blood pressure waveform measuring device 100 is fixed to a wrist 200 during the measurement of the waveform of the blood pressure of the radial artery.

The radial artery blood pressure waveform measuring device 100 includes a stress sensor 110, a stress concentrating elastic structure 120, a stress guiding elastic member 130, and an elastic band 140. The stress sensor 110 is in contact with a skin surface 210 of the wrist 200 corresponding to the position of the radial artery. The stress concentrating elastic structure 120 is disposed on the stress sensor 110. The stress guiding elastic member 130 has a top surface 132, a bottom surface 134, and at least one side surface 136. The bottom surface 134 is disposed on the stress concentrating elastic structure 120, and an area of the bottom surface 134 is greater than an area of a horizontal section of the stress concentrating elastic structure 120. The elastic band 140 surrounds the stress guiding elastic member 130 and the wrist 200 and applies a contractile force on the wrist 200, the top surface 132, and the side surface 136.

Since the measurement of the waveform of the blood pressure is more sophisticated than the measurement of the diastolic blood pressure and the systolic blood pressure, the stress sensor 110 should be disposed on the skin surface 210 of the wrist 200 at the place corresponding to the radial artery, and an appropriate amount of force should be applied on the stress sensor 110, such that the stress sensor 110 can accurately measure the waveform of the blood pressure of the radial artery. If an insufficient force is applied on the stress sensor 110, the stress sensor 110 cannot measure the waveform of the blood pressure of the radial artery with enough accuracy. If the force applied on the stress sensor 110 is too large, on the other hand, the stress sensor 110 may be damaged. In addition, the skin surface of the wrist 200 is not a uniform plane or a uniform curved surface, but an uneven surface. Moreover, some parts of the skin surface are hard, and some parts of the skin surface are soft. Therefore, if the magnitude of the force applied on the stress sensor 110 is inappropriate, the direction of the force is inaccurate, or the force is uneven, the stress sensor 110 may shift to another position, such that the stress sensor 110 can not be appropriately fixed to the skin surface 210 of the wrist 200 corresponding to the position of the radial artery, thereby resulting in an inability to effectively perform the measurement.

The radial artery blood pressure waveform measuring device 100 can solve the aforementioned problem. The elastic band 140 surrounds the stress guiding elastic member 130 and the wrist 200 and applies a contractile force on the wrist 200, the top surface 132, and the side surface 136. The stress guiding elastic member 130 receives the contractile force applied by the elastic band 140 and guides the contractile force to the stress concentrating elastic structure 120. In order to avoid bringing an uncomfortable feeling to the subject, the contractile force of the elastic band 140 should not be too large. The area of the bottom surface 134 is greater than the area of the horizontal section of the stress concentrating elastic structure 120, so that the contractile force applied on the stress guiding elastic member 130 can be concentrated on the stress concentrating elastic structure 120. Therefore, the stress concentrating elastic structure 120 can apply a sufficiently large force on the stress sensor 110, such that the measurement can be effectively performed.

A side profile of the stress guiding elastic member 130 is trapezoidal in shape. In other words, the stress guiding elastic member 130 is a trapezoidal cylinder or a trapezoidal column. When the elastic band 140 surrounds the stress guiding elastic member 130 and the wrist 200, the elastic band 140 applies the contractile force on the top surface 132 and the side surface 136. After the stress guiding elastic member 130 receives the contractile force, the stress guiding elastic member 130 guides the force to the stress concentrating elastic structure 120 via the bottom surface 134. Therefore, the stress concentrating elastic structure 120 receives the downward force, such that the stress concentrating elastic structure 120 can apply the force in the right direction on the stress sensor 110, thereby enabling the stress sensor 110 to be stably positioned in the right position to perform the measurement properly.

The radial artery blood pressure waveform measuring device 100 may further include an elastic stress buffer 150. The elastic stress buffer 150 is disposed below the bottom surface 134 and on one side of the stress concentrating elastic structure 120. The elastic stress buffer 150 buffers the contractile force applied on the side surface 136 by the elastic band 140. Since the skin surface 210 corresponding to the position of the radial artery is not located on the center of the wrist 200, the contractile force applied on the top surface 132 and the side surface 136 by the elastic band 140 is not a downward force, but a downward force combined with a sideward force. In order to avoid the sideward force from interfering with the measurement of the stress sensor 110 or from altering the position of the radial artery blood pressure waveform measuring device 100, the elastic stress buffer 150 is disposed below the bottom surface 134 and on one side of the stress concentrating elastic structure 120. Therefore, when the radial artery blood pressure waveform measuring device 100 is fixed to the wrist 200, the elastic stress buffer 150 abuts against the bottom surface 134 and the skin surface on one side of the stress concentrating elastic structure 120, such that some of the contractile force applied on the side surface 136 by the elastic band 140 is buffered to thereby enable the measurement to be properly performed.

In particular, the elastic stress buffer 150 is in the shape of a column. People having ordinary skill in the art can make proper modifications to the shape of the elastic stress buffer 150 depending on the actual application.

Moreover, a Modulus of Elasticity of the elastic stress buffer 150 is less than a Modulus of Elasticity of the stress guiding elastic member 130. More particularly, in some embodiments, the stress guiding elastic member 130 is formed of a foam material, and the elastic stress buffer 150 is formed using a sponge material. People having ordinary skill in the art can make proper modifications to the stress guiding elastic member 130 and the elastic stress buffer 150 depending on the actual application.

The stress concentrating elastic structure 120 includes a stress applying layer 122, a buffer layer 124, and a stress receiving layer 126. The stress applying layer 122 is disposed on the stress sensor 110. The buffer layer 124 is disposed on the stress applying layer 122. The stress receiving layer 126 is disposed on the buffer layer 124.

Specifically, the hardness of each of the stress applying layer 122 and the stress receiving layer 126 is greater than the hardness of the buffer layer 124. More specifically, each of the stress applying layer 122 and the stress receiving layer 126 is formed of a foam material, and the buffer layer 124 is formed of a sponge material or rubber.

Since the stress applying layer 122 applies a force on the stress sensor 110, and the stress receiving layer 126 receives a force applied by the stress guiding elastic member 130, the stress applying layer 122 and the stress receiving layer 126 should have enough hardness, such that the stress applying layer 122 can properly apply the force on the stress sensor 110 and the stress receiving layer 126 can properly receive the force applied by the stress guiding elastic member 130. The buffer layer 124 should have a certain degree of elasticity, so that the buffer layer 124 can buffer some unexpected external forces applied on the radial artery blood pressure waveform measuring device 100, thereby preventing damage to the stress sensor 110 and moving the stress sensor 110 to the wrong position.

In particular, the buffer layer 124 and the elastic stress buffer 150 can be formed as a single piece. In other words, the buffer layer 124 and the elastic stress buffer 150 can be the same element formed using a sponge material. Therefore, the manufacturing process of the radial artery blood pressure waveform measuring device 100 is made easier, and the manufacturing cost thereof may be decreased.

The stress sensor 110 may further include a sensor body 112, a gasket 114, and a wire (not shown). The sensor body 112 and the wire are disposed on the gasket 114. The wire is electrically connected to the sensor body 112 and a blood pressure waveform analyzer (not shown). The gasket 114 can protect the sensor body 112 and the wire, so as to prevent the sensor body 112 and the wire from being damaged by being directly hit by other objects.

The sensor body 112 may be a piezoelectric ceramic sensor, a piezoelectric polymer sensor, a piezoelectric stress sensor, or a piezoelectric semiconductor. People having ordinary skill in the art can make proper modifications to the sensor body 112 depending on the actual application.

The radial artery blood pressure waveform measuring device 100 can apply a force with the approximate magnitude and the right direction on the stress sensor 110, such that the stress sensor 110 can be fixed to the skin surface 210 corresponding to the position of the radial artery to thereby enable the measurement to be effectively performed. In addition, the radial artery blood pressure waveform measuring device 100 is simple to operate. When a user wants to use the radial artery blood pressure waveform measuring device 100, the user only needs to sequentially place the stress sensor 110, the stress concentrating elastic structure 120, and the stress guiding elastic member 130 on or above the skin surface 210 and then surround the elastic band 140 around the stress guiding elastic member 130 and the wrist 200. Subsequently, the radial artery blood pressure waveform measuring device 100 is positioned on the skin surface 210 at the place corresponding to the radial artery.

Moreover, the radial artery blood pressure waveform measuring device 100 is adaptable to different people. Since the stress concentrating elastic structure 120 and the stress guiding elastic member 130 are both elastic structures, and the buffer layer 124 can buffer forces, the stress concentrating elastic structure 120 and the stress guiding elastic member 130 can properly guide the contractile force of the elastic band and apply a force on the stress sensor 110 to effectively perform the measurement, even if the size of the elastic band 140 does not exactly match the wrist 200 of the subject. Furthermore, when the subject moves the wrist 200 during the measurement, such that an external force is applied on the radial artery blood pressure waveform measuring device 100, the elasticity of the stress concentrating elastic structure 120 and the stress guiding elastic member 130 is such that the stress sensor 110 is still properly positioned on the skin surface 210 at the place corresponding to the radial artery. Hence, the measurement is stable and is not affected.

Additionally, the structure of the radial artery blood pressure waveform measuring device 100 is fairly simple, so that assembly of the radial artery blood pressure waveform measuring device 100 is not difficult. Most components of the radial artery blood pressure waveform measuring device 100 are made of a foam or sponge material. Therefore, the manufacturing cost of the radial artery blood pressure waveform measuring device 100 is relatively low.

By surrounding the elastic band 140 around the stress guiding elastic member 130 and the wrist 200 to apply the contractile force on the wrist 200, the top surface 132, and the side surface 136, the stress guiding elastic member 130 receives the contractile force applied by the elastic band 140 and guides the contractile force to the stress concentrating elastic structure 120. The area of the bottom surface 134 is greater than the area of the horizontal section of the stress concentrating elastic structure 120, so that the contractile force applied to the stress guiding elastic member 130 can be concentrated on the stress concentrating elastic structure 120. Therefore, the stress concentrating elastic structure 120 can apply a sufficiently large force on the stress sensor 110, such that the stress sensor 110 is properly fixed to the skin surface 210 of the wrist 200 corresponding to the position of the radial artery, thereby enabling the measurement to be effectively performed.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. § 112, 6th paragraph. In particular, the use of "step of" in the claims herein is not intended to invoke the provisions of 35 U.S.C. § 112, 6th paragraph.

What is claimed is:

1. A radial artery blood pressure waveform measuring device, comprising:
    a stress sensor configured for contact with a skin surface of a wrist corresponding to a position of a radial artery;
    a stress concentrating elastic structure disposed on the stress sensor;
    a stress guiding elastic member having a top surface, a bottom surface, and at least one side surface, wherein the bottom surface is disposed on the stress concentrating elastic structure, and an area of the bottom surface is greater than an area of a horizontal section of the stress concentrating elastic structure; and
    an elastic stress bugger disposed below the bottom surface and on one side of the stress concentrating elastic structure, for buffering a contractile force applied on the side surface by the elastic band, wherein the elastic stress buffer is formed of a sponge material.

2. The radial artery blood pressure waveform measuring device of claim 1, further comprising an elastic band surrounding the stress guiding elastic member and being configured to surround the wrist, and capable of applying the contractile force on the wrist, the top surface, and the side surface.

3. The radial artery blood pressure waveform measuring device of claim 1, wherein a Modulus of Elasticity of the elastic stress buffer is less than a Modulus of Elasticity of the stress guiding elastic member.

4. The radial artery blood pressure waveform measuring device of claim 1, wherein a side profile of the stress guiding elastic member is trapezoidal in shape.

5. The radial artery blood pressure waveform measuring device of claim 1, wherein the stress guiding elastic member is formed of a foam material.

6. The radial artery blood pressure waveform measuring device of claim 1, wherein the stress concentrating elastic structure comprises:
    a stress applying layer disposed on the stress sensor;
    a buffer layer disposed on the stress applying layer; and
    a stress receiving layer disposed on the buffer layer.

7. The radial artery blood pressure waveform measuring device of claim 6, wherein each of the stress applying layer and the stress receiving layer is formed of a foam material.

8. The radial artery blood pressure waveform measuring device of claim 6, wherein the buffer layer is formed of a sponge material or rubber.

* * * * *